(12) United States Patent  
Ruegger et al.

(10) Patent No.: US 8,673,918 B2  
(45) Date of Patent: Mar. 18, 2014

(54) COMPOSITIONS COMPRISING SPHINGOSINE 1 PHOSPHATE (S1P) RECEPTOR MODULATORS

(75) Inventors: Colleen Ruegger, Morris Plains, NJ (US); Michael Ambühl, Rheinfelden (CH)

(73) Assignee: Novartis AG, Basel (CH)

( * ) Notice: Subject to any disclaimer, the term of this patent is extended or adjusted under 35 U.S.C. 154(b) by 418 days.

(21) Appl. No.: 12/682,343

(22) PCT Filed: Oct. 9, 2008

(86) PCT No.: PCT/US2008/079264
§ 371 (c)(1),
(2), (4) Date: Jun. 9, 2010

(87) PCT Pub. No.: WO2009/048993
PCT Pub. Date: Apr. 16, 2009

(65) Prior Publication Data
US 2010/0267675 A1    Oct. 21, 2010

Related U.S. Application Data

(60) Provisional application No. 60/979,482, filed on Oct. 12, 2007.

(51) Int. Cl.
*A61K 31/497* (2006.01)
*A61K 31/44* (2006.01)
*A61K 31/425* (2006.01)

(52) U.S. Cl.
USPC .................... 514/252.1; 514/357; 514/372

(58) Field of Classification Search
USPC ...................... 514/252.1, 357, 372
See application file for complete search history.

(56) References Cited

U.S. PATENT DOCUMENTS 5,604,229 A * 2/1997 Fujita et al. ............ 514/252.1

FOREIGN PATENT DOCUMENTS

| EP | 627406 A1 * | 12/1994 |
| EP | 0990440 A1 | 4/2000 |
| WO | WO 02/18395 A1 | 3/2002 |
| WO | WO 2004/089341 A1 | 10/2004 |
| WO | WO 2004/103306 | 12/2004 |
| WO | 2005025553 A2 | 3/2005 |
| WO | WO 2007/021666 | 2/2007 |
| WO | WO 2008/037421 A2 | 4/2008 |

OTHER PUBLICATIONS

Loginova N.V., Polpzov G.I. Introduction in Pharmaceutical Chemistry, Minsk, BGU, p. 88, lines 15-20, 2003 (English translation of cover page and relevant sections).
Kappos et al., "Oral Fingolimod (FTY720) for Relapsing Multiple Sclerosis", New England Journal of Medicine, vol. 355 (11), pp. 1124-1140, (Sep. 14, 2006).
Kappos et al., Commented by Morten Blinkenberg, Oct. 26, 2006. "Oral fingolimod (FTY720) for relapsing multiple sclerosis", New England Journal of Medicine, vol. 355 (11), pp. 1124-1140, (Sep. 14, 2006) . Lundbeck Institite / CNSforum / Commented Articles via http://www.cnsforum.com/commenteditem/B3F6ADBD-9CD5-4AD1-A272-22F98C744AFE/default.aspx, (2006).

* cited by examiner

*Primary Examiner* — Kevin E Weddington
(74) *Attorney, Agent, or Firm* — Andrew Holmes

(57) ABSTRACT

The present invention relates to stable compositions comprising a sphingosine 1 phosphate (S1P) receptor modulator, suitable for use as a dosage form. The S1P receptor modulators are typically sphingosine analogues, such as 2-substituted 2-amino-propane-1,3-diol or 2-amino-propanol derivatives, e.g. a compound comprising a group of formula Y.

13 Claims, No Drawings

COMPOSITIONS COMPRISING SPHINGOSINE 1 PHOSPHATE (S1P) RECEPTOR MODULATORS

This is a National Stage of International Application No. PCT/US2008/079264 filed on Oct. 9, 2008, which claims benefit of U.S. Provisional Application No. 60/979,482 filed Oct. 12, 2007, which in its entirety are herein incorporated by reference.

The present invention relates to a composition comprising a sphingosine 1 phosphate (S1P) receptor modulator.

In particular, the present invention relates to stable compositions comprising a sphingosine 1 phosphate (S1P) receptor modulator suitable for use as a dosage form.

S1P receptor modulators are typically sphingosine analogues, such as 2-substituted 2-amino-propane-1,3-diol or 2-amino-propanol derivatives, e.g. a compound comprising a group of formula Y.

S1P Receptor Modulators

Sphingosine-1 phosphate (hereinafter "S1P") is a natural serum lipid. Presently there are eight known S1P receptors, namely S1P1 to S1P8. S1P receptor modulators are typically sphingosine analogues, such as 2-substituted 2-amino-propane-1,3-diol or 2-amino-propanol derivatives, e.g. a compound comprising a group of formula Y

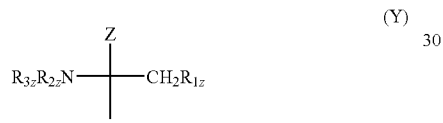

wherein Z is H, $C_{1-6}$alkyl, $C_{2-6}$alkenyl, $C_{2-6}$alkynyl, phenyl, phenyl substituted by OH, $C_{1-6}$alkyl substituted by 1 to 3 substituents selected from the group consisting of halogen, $C_{3-8}$cycloalkyl, phenyl and phenyl substituted by OH, or $CH_2$—$R_{4z}$ wherein $R_{4z}$ is OH, acyloxy or a residue of formula (a)

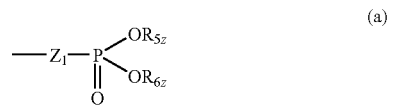

wherein $Z_1$ is a direct bond or O, preferably O;
each of $R_{5z}$ and $R_{6z}$, independently, is H, or $C_{1-4}$alkyl optionally substituted by 1, 2 or 3 halogen atoms;
$R_{1z}$ is OH, acyloxy or a residue of formula (a); and each of $R_{2z}$ and $R_{3z}$ independently, is H, $C_{1-4}$alkyl or acyl.

Group of formula Y is a functional group attached as a terminal group to a moiety which may be hydrophilic or lipophilic and comprise one or more aliphatic, alicyclic, aromatic and/or heterocyclic residues, to the extent that the resulting molecule wherein at least one of Z and $R_{1z}$ is or comprises a residue of formula (a), signals as an agonist at one of more sphingosine-1-phosphate receptor.

S1P receptor modulators are compounds which signal as agonists at one or more sphingosine-1 phosphate receptors, e.g. S1P1 to S1P8. Agonist binding to a S1P receptor may e.g. result in dissociation of intracellular heterotrimeric G-proteins into Gα-GTP and Gβγ-GTP, and/or increased phosphorylation of the agonist-occupied receptor and activation of downstream signaling pathways/kinases.

Examples of appropriate S1P receptor modulators, comprising a group of formula Y are, for example:

Compounds as disclosed in EP627406A1, e.g. a compound of formula I

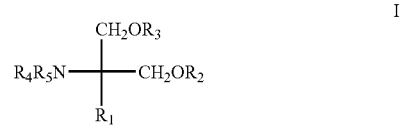

wherein $R_1$ is a straight- or branched ($C_{12-22}$)chain
which may have in the chain a bond or a hetero atom selected from a double bond, a triple bond, O, S, $NR_6$, wherein $R_6$ is H, aryl-$C_{1-4}$alkyl, acyl or ($C_{1-4}$alkoxy) carbonyl, and carbonyl, and/or
which may have as a substituent $C_{1-4}$alkoxy, $C_{2-4}$alkenyloxy, $C_{2-4}$alkynyloxy, aryl$C_{1-4}$alkyl-oxy, acyl, $C_{1-4}$alkylamino, $C_{1-4}$alkylthio, acylamino, ($C_{1-4}$alkoxy)carbonyl, ($C_{1-4}$alkoxy)-carbonylamino, acyloxy, ($C_{1-4}$alkyl)carbamoyl, nitro, halogen, amino, hydroxyimino, hydroxy or carboxy; or $R_1$ is
a phenylalkyl wherein alkyl is a straight- or branched ($C_{6-20}$)carbon chain; or
a phenylalkyl wherein alkyl is a straight- or branched ($C_{1-30}$)carbon chain wherein said phenylalkyl is substituted by
a straight- or branched ($C_{6-20}$)carbon chain optionally substituted by halogen,
a straight- or branched ($C_{6-20}$)alkoxy chain optionally substituted by halogen,
a straight- or branched ($C_{6-20}$)alkenyloxy,
phenyl-$C_{1-14}$alkoxy, halophenyl-$C_{1-4}$alkoxy, phenyl-$C_{1-14}$alkoxy-$C_{1-14}$alkyl, phenoxy-$C_{1-4}$alkoxy or phenoxy-$C_{1-4}$alkyl,
cycloalkylalkyl substituted by $C_{6-20}$alkyl,
heteroarylalkyl substituted by $C_{6-20}$alkyl,
heterocyclic $C_{6-20}$alkyl or
heterocyclic alkyl substituted by $C_{2-20}$alkyl,
and wherein
the alkyl moiety may have
in the carbon chain, a bond or a heteroatom selected from a double bond, a triple bond, O, S, sulfinyl, sulfonyl, or $NR_6$, wherein $R_6$ is as defined above, and
as a substituent $C_{1-4}$alkoxy, $C_{2-4}$alkenyloxy, $C_{2-4}$alkynyloxy, aryl$C_{1-4}$alkyloxy, acyl, $C_{1-4}$alkyl-amino, $C_{1-4}$alkylthio, acylamino, ($C_{1-4}$alkoxy)carbonyl, ($C_{1-4}$alkoxy) carbonylamino, acyloxy, ($C_{1-4}$alkyl)carbamoyl, nitro, halogen, amino, hydroxy or carboxy, and
each of $R_2$, $R_3$, $R_4$ and $R_5$, independently, is H, $C_{1-4}$ alkyl or acyl
or a pharmaceutically acceptable salt or hydrate thereof;

Compounds as disclosed in EP 1002792A1, e.g. a compound of formula II

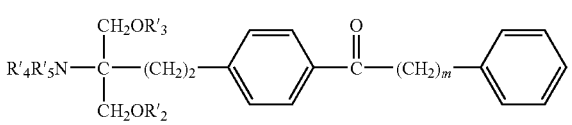

wherein m is 1 to 9 and each of $R'_2$, $R'_4$ and $R'_5$, independently, is H, $C_{1-6}$alkyl or acyl,
or a pharmaceutically acceptable salt or hydrate thereof;

Compounds as disclosed in EP0778263 A1, e.g. a compound of formula III

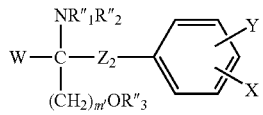

wherein W is H; C$_{1-6}$alkyl, C$_{2-6}$alkenyl or C$_{2-6}$alkynyl; unsubstituted or by OH substituted phenyl; R″$_4$O(CH$_2$)$_n$; or C$_{1-6}$alkyl substituted by 1 to 3 substituents selected from the group consisting of halogen, C$_{3-8}$cycloalkyl, phenyl and phenyl substituted by OH;
X is H or unsubstituted or substituted straight chain alkyl having a number p of carbon atoms or unsubstituted or substituted straight chain alkoxy having a number (p−1) of carbon atoms, e.g. substituted by 1 to 3 substituents selected from the group consisting of C$_{1-6}$alkyl, OH, C$_{1-6}$alkoxy, acyloxy, amino, C$_{1-6}$alkylamino, acylamino, oxo, haloC$_{1-6}$alkyl, halogen, unsubstituted phenyl and phenyl substituted by 1 to 3 substituents selected from the group consisting of C$_{1-6}$alkyl, OH, C$_{1-6}$alkoxy, acyl, acyloxy, amino, C$_{1-6}$alkylamino, acylamino, haloC$_{1-6}$alkyl and halogen; Y is H, C$_{1-6}$alkyl, OH, C$_{1-6}$alkoxy, acyl, acyloxy, amino, C$_{1-6}$alkylamino, acylamino, haloC$_{1-6}$alkyl or halogen, Z$_2$ is a single bond or a straight chain alkylene having a number or carbon atoms of q, each of p and q, independently, is an integer of 1 to 20, with the proviso of 6≤p+q≤23, m' is 1, 2 or 3, n is 2 or 3,
each of R″$_1$, R″$_2$, R″$_3$ and R″$_4$, independently, is H, C$_{1-4}$alkyl or acyl,
or a pharmaceutically acceptable salt or hydrate thereof,
Compounds as disclosed in WO02/18395, e.g. a compound of formula IVa or IVb

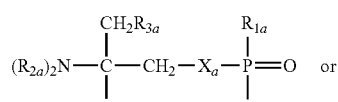

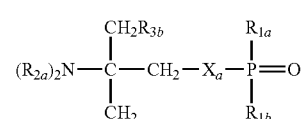

wherein X$_a$ is O, S, NR$_{1s}$ or a group —(CH$_2$)$_{na}$—, which group is unsubstituted or substituted by 1 to 4 halogen; n$_a$ is 1 or 2, R$_{1s}$ is H or (C$_{1-4}$)alkyl, which alkyl is unsubstituted or substituted by halogen; R$_{1a}$ is H, OH, (C$_{1-4}$)alkyl or O(C$_{1-4}$)alkyl wherein alkyl is unsubstituted or substituted by 1 to 3 halogen; R$_{1b}$ is H, OH or (C$_{1-4}$)alkyl, wherein alkyl is unsubstituted or substituted by halogen; each R$_{2a}$ is independently selected from H or (C$_{1-4}$)alkyl, which alkyl is unsubstituted or substituted by halogen; R$_{1a}$ is H, OH, halogen or O(C$_{1-4}$)alkyl wherein alkyl is unsubstituted or substituted by halogen; and R$_{3b}$ is H, OH, halogen, (C$_{1-4}$)alkyl wherein alkyl is unsubstituted or substituted by hydroxy, or O(C$_{1-4}$)alkyl wherein alkyl is unsubstituted or substituted by halogen; Y$_a$ is —CH$_2$—, —C(O)—, —CH(OH)—, —C(=NOH)—, O or S, and R$_{4a}$ is (C$_{4-14}$)alkyl or (C$_{4-14}$)alkenyl;
or a pharmaceutically acceptable salt or hydrate thereof;
Amino alcohol compounds of formula V

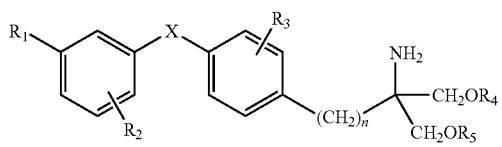

wherein X is O, S, SO or SO$_2$;
R$_1$ is halogen, trihalomethyl, OH, C$_{1-7}$alkyl, C$_{1-4}$alkoxy, trifluoromethoxy, phenoxy, cyclohexylmethyloxy, pyridylmethoxy, cinnamyloxy, naphthyl methoxy, phenoxymethyl, CH$_2$—OH, CH$_2$—CH$_2$—OH, C$_{1-4}$alkylthio, C$_{1-4}$alkylsulfonyl, benzylthio, acetyl, nitro or cyano, or phenyl, phenylC$_{1-4}$alkyl or phenyl-C$_{1-4}$alkoxy each phenyl group thereof being optionally substituted by halogen, CF$_3$, C$_{1-4}$alkyl or C$_{1-4}$alkoxy;
R$_2$ is H, halogen, trihalomethyl, C$_{1-4}$alkoxy, phenethyl or benzyloxy;
R$_3$H, halogen, CF$_3$, OH, C$_{1-7}$alkyl, C$_{1-4}$alkoxy, benzyloxy, phenyl or C$_{1-4}$alkoxymethyl;
each of R$_4$ and R$_5$, independently is H or a residue of formula (a)

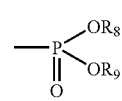

wherein each of R$_8$ and R$_9$, independently, is H or C$_{1-4}$alkyl optionally substituted by halogen; and
n is an integer from 1 to 4;
or a pharmaceutically acceptable salt thereof;
or a compound of formula VI

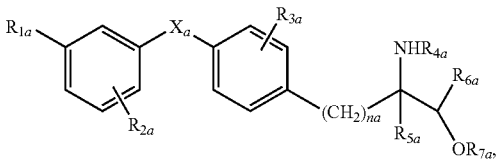

wherein
R$_{1a}$ is halogen, trihalomethyl, C$_{1-4}$alkyl, C$_{1-4}$alkylsulifinyl, C$_{1-4}$alkyl-sulfonyl, aralkyl, optionally substituted phenoxy or aralkyloxy;

$R_{2a}$ is H, halogen, trihalomethyl, $C_{1-4}$alkoxy, aralkyl or aralkyloxy;

$R_{3a}$ is H, halogen, $CF_3$, $C_{1-4}$alkyl, $C_{1-4}$alkoxy, $C_{1-4}$alkylthio or benzyloxy;

$R_{4a}$ is H, $C_{1-4}$alkyl, phenyl, optionally substituted benzyl or benzoyl, or lower aliphatic $C_{1-5}$acyl;

$R_{5a}$ is H, monohalomethyl, $C_{1-4}$alkoxy-methyl, $C_{1-4}$alkylthiomethyl, hydroxyethyl, hydroxypropyl, phenyl, aralkyl, $C_{2-4}$alkenyl or -alkynyl;

$R_{6a}$ is H or $C_{1-4}$alkyl;

$R_{7a}$ is H, $C_{1-4}$alkyl or a residue of formula (a) as defined above, $X_a$ is O, S, SO or $SO_2$; and $n_a$ is an integer of 1 to 4;

or a pharmaceutically acceptable salt thereof.

With regard to the compounds of formulae (I) and (II), the term "halogen" encompasses fluorine, chlorine, bromine and iodine. The term "trihalomethyl group" encompasses trifluoromethyl and trichloromethyl. "$C_{1-7}$ alkyl" encompasses straight-chained or branched alkyl, e.g. methyl, ethyl, propyl, isopropyl, butyl, t-butyl, pentyl, hexyl or heptyl. The phrase "substituted or unsubstituted phenoxy group" encompasses those that have, at any position of its benzene ring, a halogen atom, such as fluorine, chlorine, bromine and iodine, trifluoromethyl, $C_{1-4}$alkyl or $C_{1-4}$alkoxy. The term "aralkyl group" as in "aralkyl group" or "aralkyloxy group" encompasses benzyl, diphenylmethyl, phenethyl and phenylpropyl. Any alkyl moiety as present in "$C_{1-4}$alkoxy", "$C_{1-4}$alkylthio", "$C_{1-4}$alkylsulfinyl" or "$C_{1-4}$alkylsulfonyl encompasses straight-chained or branched $C_{1-4}$alkyl, e.g. methyl, ethyl, propyl, isopropyl or butyl. The phrase "substituted or unsubstituted aralkyl group" encompasses those that have, at any position of its benzene ring, a halogen atom, such as fluorine, chlorine, bromine and iodine, trifluoromethyl, lower alkyl having 1-4 carbon atoms, or lower alkoxy having 1-4 carbon atoms.

Other compounds of formula V are compounds of formula Va

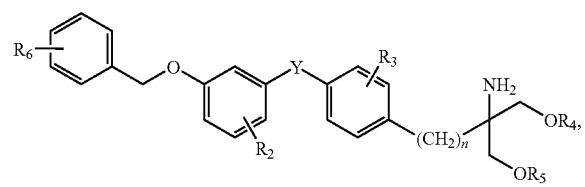

(Va)

wherein $R_2$, $R_3$, $R_4$, $R_5$ and n are as defined above; and Y is O or S and $R_6$ is hydrogen, halogen, $C_{1-7}$alkyl, $C_{1-4}$alkoxy or trifluoromethyl.

Compounds of formulae V and Va are known and are disclosed e.g. in WO03/029205, WO 03/029184 and WO04/026817, respectively, the phosphorylated derivatives being disclosed e.g. in WO04/074297, the contents of which being incorporated herein by reference in their entirety. Compounds disclosed may be prepared as disclosed in the cited references herein.

Phosphorylated derivatives of compounds described herein can be prepared utilizing the procedures for synthesizing phosphorylated compounds described known in the art, e.g., in WO 2005/021503 (see, e.g., pages 11 and 12).

Optically active compounds of and phosphorylated derivatives thereof can be prepared in high purity utilizing procedure described in the art, e.g. in Hinterding et al., *Synthesis*, Vol. 11, pp. 1667-1670 (2003).

Compounds as disclosed in WO02/06268A1, e.g. a compound of formula VI

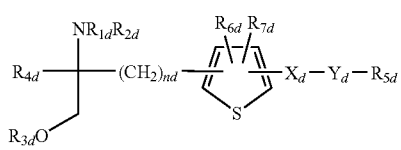

VI wherein each of $R_{1d}$ and $R_{2d}$, independently, is H or an amino-protecting group;

$R_{3d}$ is hydrogen, a hydroxy-protecting group or a residue of formula

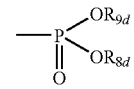

$R_{4d}$ is $C_{1-4}$alkyl;

$n_d$ is an integer of 1 to 6;

$X_d$ is ethylene, vinylene, ethynylene, a group having a formula -D-$CH_2$— (wherein D is carbonyl, —CH(OH)—, O, S or N), aryl or aryl substituted by up to three substituents selected from group a as defined hereinafter;

$Y_d$ is single bond, $C_{1-10}$alkylene, $C_{1-10}$alkylene which is substituted by up to three substituents selected from groups a and b, $C_{1-10}$alkylene having O or S in the middle or end of the carbon chain, or $C_{1-10}$alkylene having O or S in the middle or end of the carbon chain which is substituted by up to three substituents selected from groups a and b;

$R_{5d}$ is hydrogen, $C_{3-6}$cycloalkyl, aryl, heterocyclic group, $C_{3-6}$cycloalkyl substituted by up to three substituents selected from groups a and b, aryl substituted by up to three substituents selected from groups a and b, or heterocyclic group substituted by up to three substituents selected from groups a and b;

each of $R_{6d}$ and $R_{7d}$, independently, is H or a substituents selected from group a;

each of $R_{8d}$ and $R_{9d}$, independently, is H or $C_{1-4}$alkyl optionally substituted by halogen;

<group a> is halogen, lower alkyl, halogeno lower alkyl, lower alkoxy, lower alkylthio, carboxyl, lower alkoxycarbonyl, hydroxy, lower aliphatic acyl, amino, mono-lower alkylamino, di-$C_{1-4}$alkylamino, acylamino, cyano or nitro; and <group b> is $C_{3-6}$cycloalkyl, aryl or heterocyclic group, each being optionally substituted by up to three substituents selected from group a;

with the proviso that when $R_{5d}$ is hydrogen, $Y_d$ is a either a single bond or linear $C_{1-10}$ alkylene, or a pharmacologically acceptable salt, ester or hydrate thereof;

Compounds as disclosed in JP-14316985 (JP2002316985), e.g. a compound of formula VII

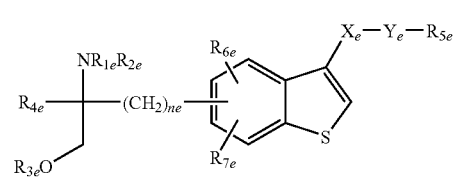

VII wherein $R_{1e}$, $R_{2e}$, $R_{3e}$, $R_{4e}$, $R_{5e}$, $R_{6e}$, $R_{7e}$, $n_e$, $X_e$ and $Y_e$ are as disclosed in JP-14316985;

or a pharmacologically acceptable salt, ester or hydrate thereof;

Compounds as disclosed in WO03/062252A1, e.g. a compound of formula VIII

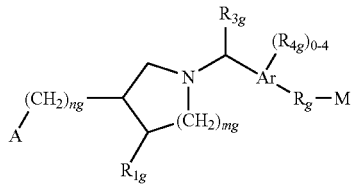

VIII wherein
Ar is phenyl or naphthyl; each of $m_g$ and $n_g$ independently is 0 or 1; A is selected from COOH, $PO_3H_2$, $PO_2H$, $SO_3H$, $PO(C_{1-3}alkyl)OH$ and 1H-tetrazol-5-yl; each of $R_{1g}$ and $R_{2g}$ independently is H, halogen, OH, COOH or $C_{1-4}$alkyl optionally substituted by halogen; $R_{3g}$ is H or $C_{1-4}$alkyl optionally substituted by halogen or OH; each $R_{4g}$ independently is halogen, or optionally halogen substituted $C_{1-4}$alkyl or $C_{1-3}$alkoxy; and each of $R_g$ and M has one of the significances as indicated for B and C, respectively, in WO03/062252A1; or a pharmacologically acceptable salt, solvate or hydrate thereof;

Compounds as disclosed in WO 031062248A2, e.g. a compound of formula IX

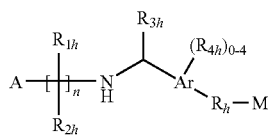

IX wherein Ar is phenyl or naphthyl; n is 2, 3 or 4; A is COOH, 1H-tetrazol-5-yl, $PO_3H_2$, $PO_2H_2$, —$SO_3H$ or $PO(R_{5h})OH$ wherein $R_{5h}$ is selected from $C_{1-4}$alkyl, hydroxy$C_{1-4}$alkyl, phenyl, —CO—$C_{1-3}$alkoxy and —CH(OH)-phenyl wherein said phenyl or phenyl moiety is optionally substituted; each of $R_{1h}$ and $R_{2h}$ independently is H, halogen, OH, COOH, or optionally halogeno substituted $C_{1-6}$alkyl or phenyl; $R_{3h}$ is H or $C_{1-4}$alkyl optionally substituted by halogen and/ OH; each $R_{4h}$ independently is halogen, OH, COOH, $S(O)_{0,1\ or\ 2}C_{1-3}$alkyl, $C_{1-3}$alkoxy, $C_{3-6}$cycloalkoxy, aryl or aralkoxy, wherein the alkyl portions may optionally be substituted by 1-3 halogens; and each of $R_h$ and M has one of the significances as indicated for B and C, respectively, in WO03/062248A2 or a pharmacologically acceptable salt, solvate or hydrate thereof.

Compounds as disclosed in WO 04/103306A, WO 05/000833, WO 05/103309 or WO 05/113330, e.g. compounds of formula Xa or Xb

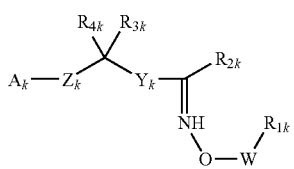

Xa

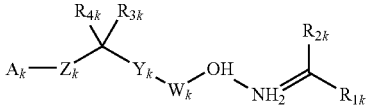

Xb wherein
$A_k$ is $COOR_{5k}$, $OPO(OR_{5k})_2$, $PO(OR_{5k})_2$, $SO_2OR_{5k}$, $POR_{5k}OR_{5k}$ or 1H-tetrazol-5-yl, $R_{5k}$ being H or $C_{1-6}$alkyl;
$W_k$ is a bond, $C_{1-3}$alkylene or $C_{2-3}$alkenylene;
$Y_k$ is $C_{6-10}$aryl or $C_{3-6}$heteroaryl, optionally substituted by 1 to 3 radicals selected from halogene, OH, $NO_2$, $C_{1-6}$alkyl, $C_{1-6}$alkoxy; halo-substituted $C_{1-6}$alkyl and halo-substituted $C_{1-6}$alkoxy;
$Z_k$ is a heterocyclic group as indicated in WO 04/103306A, e.g. azetidine;
$R_{1k}$ is $C_{6-10}$aryl or $C_{3-9}$heteroaryl, optionally substituted by $C_{1-6}$alkyl, $C_{6-10}$aryl, $C_{6-10}$aryl$C_{1-4}$alkyl, $C_{3-9}$heteroaryl, $C_{3-9}$heteroaryl$C_{1-4}$alkyl, $C_{3-8}$cycloalkyl, $C_{3-8}$cycloalkyl$C_{1-4}$alkyl, $C_{3-8}$heterocycloalkyl or $C_{3-8}$heterocycloalkyl$C_{1-4}$alkyl; wherein any aryl, heteroaryl, cycloalkyl or heterocycloalkyl of $R_{1k}$ may be substituted by 1 to 5 groups selected from halogen, $C_{1-6}$alkyl, $C_{1-6}$alkoxy and halo substituted-$C_{1-6}$alkyl or —$C_{1-6}$alkoxy;
$R_{2k}$ is H, $C_{1-6}$alkyl, halo substituted $C_{1-6}$alkyl, $C_{2-6}$alkenyl or $C_{2-6}$alkynyl: and
each of $R_{1k}$ or $R_{4k}$, independently, is H, halogen, OH, $C_{1-6}$alkyl, $C_{1-6}$alkoxy or halo substituted $C_{1-6}$alkyl or $C_{1-6}$alkoxy;
and the N-oxide derivatives thereof or prodrugs thereof, or a pharmacologically acceptable salt, solvate or hydrate thereof.

The compounds of formulae I to Xb may exist in free or salt form. Examples of pharmaceutically acceptable salts of the compounds of the formulae III to VIII include salts with inorganic acids, such as hydrochloride, hydrobromide and sulfate, salts with organic acids, such as acetate, fumarate, maleate, benzoate, citrate, malate, methanesulfonate and benzenesulfonate salts, or, when appropriate, salts with metals such as sodium, potassium, calcium and aluminium, salts with amines, such as triethylamine and salts with dibasic amino acids, such as lysine. The compounds and salts of the combination of the present invention encompass hydrate and solvate forms.

Acyl as indicated above may be a residue $R_y$—CO— wherein $R_y$ is $C_{1-6}$alkyl, $C_{3-6}$cycloalkyl, phenyl or phenyl-$C_{1-4}$ alkyl. Unless otherwise stated, alkyl, alkoxy, alkenyl or alkynyl may be straight or branched.

Aryl may be phenyl or naphthyl, preferably phenyl.

When in the compounds of formula I the carbon chain as $R_1$ is substituted, it is preferably substituted by halogen, nitro, amino, hydroxy or carboxy. When the carbon chain is interrupted by an optionally substituted phenylene, the carbon chain is preferably unsubstituted. When the phenylene moiety is substituted, it is preferably substituted by halogen, nitro, amino, methoxy, hydroxy or carboxy.

Preferred compounds of formula I are those wherein $R_1$ is $C_{13-20}$alkyl, optionally substituted by nitro, halogen, amino, hydroxy or carboxy, and, more preferably those wherein $R_1$ is phenylalkyl substituted by $C_{6-14}$-alkyl chain optionally substituted by halogen and the alkyl moiety is a $C_{1-6}$alkyl optionally substituted by hydroxy. More preferably, $R_1$ is phenyl-$C_{1-6}$alkyl substituted on the phenyl by a straight or branched, preferably straight, $C_{6-14}$alkyl chain. The $C_{6-14}$alkyl chain may be in ortho, meta or para, preferably in para.

Preferably each of $R_2$ to $R_5$ is H.

In the above formula of VII "heterocyclic group" represents a 5- to 7 membered heterocyclic group having 1 to 3 heteroatoms selected from S, O and N. Examples of such heterocyclic groups include the heteroaryl groups indicated above, and heterocyclic compounds corresponding to partially or completely hydrogenated heteroaryl groups, e.g. furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl, pyrazinyl, tetrahydropyranyl, morpholinyl, thiomorpholinyl, pyrrolidinyl, pyrrolyl, imidazolidinyl, pyrazolidinyl, piperidinyl, piperazinyl, oxazolidinyl, isoxazolidinyl, thiazolidinyl or pyrazolidinyl. Preferred heterocyclic groups are 5- or 6-membered heteroaryl groups and the most preferred heteocyclic group is a morpholinyl, thiomorpholinyl or piperidinyl group.

A preferred compound of formula I is 2-amino-2-tetradecyl-1,3-propanediol. A particularly preferred S1P receptor agonist of formula III is FTY720, i.e. 2-amino-2-[2-(4-octylphenyl)ethyl]propane-1,3-diol in free form or in a pharmaceutically acceptable salt form (referred to hereinafter as Compound A), e.g. the hydrochloride, as shown:

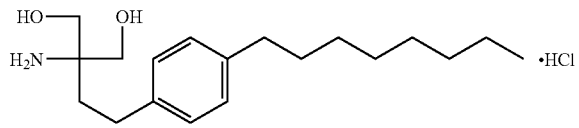 [SMILES: CCCCCCCCc1ccc(CCC(N)(CO)CO)cc1 ; Cl]

A preferred compound of formula II is the one wherein each of $R'_2$ to $R'_5$ is H and m is 4, i.e. 2-amino-2-{2-[4-(1-oxo-5-phenylpentyl)phenyl]ethyl}propane-1,3-diol, in free form or in pharmaceutically acceptable salt form (referred to hereinafter as Compound B), e.g the hydrochloride.

A preferred compound of formula III is the one wherein W is $CH_3$, each of $R''_1$ to $R''_3$ is H, $Z_2$ is ethylene, X is heptyloxy and Y is H, i.e. 2-amino-4-(4-heptyloxyphenyl)-2-methylbutanol, in free form or in pharmaceutically acceptable salt form (referred to hereinafter as Compound C), e.g. the hydrochloride. The R-enantiomer is particularly preferred.

A preferred compound of formula IVa is the FTY720-phosphate ($R_{2a}$ is H, $R_{3a}$ is OH, $X_a$ is O, $R_{1a}$ and $R_{1b}$ are OH). A preferred compound of formula IVb is the Compound C-phosphate ($R_{2a}$ is H, $R_{3b}$ is OH, $X_a$ is O, $R_{1a}$ and $R_{1b}$ are OH, $Y_a$ is O and $R_{4a}$ is heptyl). A preferred compound of formula V is Compound B-phosphate.

A preferred compound of formula VII is (2R)-2-amino-4-[3-(4-cyclohexyloxybutyl)-benzo[b]thien-6-yl]-2-methylbutan-1-ol.

A preferred compound of formula Xa is e.g. 1-{4-[1-(4-cyclohexyl-3-trifluoromethyl-benzyloxyimino)-ethyl]-2-ethyl-benzyl}-azetidine-3-carboxylic acid, or a prodrug thereof.

It will be appreciated that the compounds as described herein may be the direct active substances, or may be prodrugs. For example, the compounds may be phosphorylated forms.

Oral Formulations

The dosage form of a composition of the present invention, e.g. the final dosage form, may be a solid dosage form, e.g. a tablet. In another embodiment of the present invention the dosage form is granular, e.g. powder form and may comprise part of a suspension or gel. Another dosage forms may comprise of small multiparticulate pellets/beads. Other dosage forms may comprise a solid or granular composition which is soluble in a liquid to produce a liquid formulation prior to administration. Examples of such formulations are soluble tablets, capsules and sachets. The final liquid formulation may be consumed as a drink.

The oral route is often the most convenient route for drug administration. This may be in the form of a standard tablet, a conventional orally disintegrating tablet, a lyophilized tablet, or a thin film.

It has been found that compounds comprising a group of formula Y, e.g. amino-propane-1,3-diols, e.g. those that have S1P agonist activity, are not easy to formulate. In particular, these are not easy to formulate in a solid oral formulation.

As such, the present inventors have surprisingly found that only a limited number of excipients are potentially feasible with such amino diols.

The Maillard Reaction

The Maillard reaction is a chemical reaction between an amino acid and a reducing sugar [Sugars that contain aldehyde groups that are oxidised to carboxylic acids are classified as reducing sugars.

Reducing sugars include glucose, glyceraldehyde, lactose, arabinose and maltose], usually requiring the addition of heat. Like caramelization, it is a form of non-enzymatic browning. The reactive carbonyl group of the sugar interacts with the nucleophilic amino group of the amino acid, and interesting but poorly characterized odor and flavor molecules result. This process accelerates in an alkaline environment because the amino groups do not neutralize. This reaction is the basis of the flavouring industry, since the type of amino acid determines the resulting flavour.

The potentially feasible excipients are classified into e.g. fillers, binders, disintegrants, lubricants, flow regulators, plastisizers, and matrix formers. Some excipients can be listed in more than one class.

Typical ranges found in a final formulation comprising a compound as described herein are as follows:

Fillers: 10-97%
Binders: 1-15%
Disintegrants: 1-15%
Lubricants: 0.5-2%
Flow regulators: 0.5-3%
Matrix formers: 3-50%
Plastisizers: 5-30%
Flavoring agents: 1-20%
Sweeteners: 1-20%

The present invention therefore relates to stable blends comprising a compound having a group of formula Y and at least one other excipient.

The compound having a group of formula Y may, in one embodiment, be mixed together with one or more of the following excipients:

(a) Fillers selected from Lactose monohydrate, Lactose anhydrous, Maize starch, Mannitol, Xylitol, sorbitol, sucrose, Microcrystalline cellulose, e.g. Avicel PH101, Dibasic calcium phosphate, Maltodextrin, gelatin, e.g. DE 12 and/or (b) Binders selected from HPMC, e.g. 3cPs, L-HPC, e.g. HP-Cellulose LH-22, Povidone.

and/or (c) Disintegrants selected from Maize starch, Crospovidone, Croscarmellose sodium, Sodium carboxymethylstarch e.g. Primojel, pregelatinized starch, e.g. Starch 1500 (Sta RX), calcium silicate and/or (d) Lubricants selected from Hydrogenated e.g. ricinoleic, castor oil, e.g. Cutina, magnesium stearate, calcium stearate, zinc stearate, mineral oil, silicone fluid, sodium lauryl sulfate, L-leucine, sodium stearyl fumarate,
and/or
(e) Flow regulators selected from Aerosil 200Colloidal silicone dioxide, e.g. Aerosil 200, Talc
and/or
(f) Matrix formers selected from Hydroxypropyl methyl cellulose, Hydroxypropyl cellulose, Methyl cellulose, Ethyl cellulose, Pullulan, Starch, e.g. Pure Cote, Povidone
and/or
(g) Plastisizers selected from PEG 400, Dibutyl sebacate, Sorbitol
and/or
(h) Flavoring agents selected from Menthol, tutti fruti
and/or
(i) Sweeteners selected from Sucralose, Sodium saccharine.

Fillers are preferably selected from Fillers selected from Lactose monohydrate, Lactose anhydrous, Maize starch, Xylitol, sorbitol, sucrose, Microcrystalline cellulose, e.g. Avicel PH101, Dibasic calcium phosphate, Maltodextrin and gelatin.

According to one embodiment of the invention preferred fubricants are selected from magnesium stearate and calcium stearate.

In a second embodiment, the present invention relates to a binary blend comprising a compound having a group of formula Y and one excipient selected from:

Sorbitol, Xylitol, dicalcium phosphate, Lactose, microcrystalline cellulose, HPMC, HPC, Crospovidone, croscarmellose sodium, starch, preferably an hydrous, calcium silicate, colloidal silicone dioxide, talc, magnesium stearate, calcium stearate.

Preferably, no moisture is present.

In particular, the excipients are selected from:

Dicalcium phosphate, HPC, crospovidone, calcium silicate, magnesium stearate.

In particular, the formulation or blend of the present invention does not comprise a reducing sugar, e.g glucose, glyceraldehyde, lactose, arabinose and maltose.

In a further preference, the formulation or blend of the present invention does not comprise PEG, stearic acid, Where necessary, stabilizers may be added to increase or decrease the pH. By modifying the pH, the composition may be adapted to optimize the reduction of likelihood of a malliard reaction, or other side reactions taking place. An example of a stabilizer is citric acid.

In a preferred embodiment of the compositions of the present invention are binary blends, i.e. a mixture of a compound comprising a group of formula Y and one excipient as listed herein.

A particular advantage of the stable binary blends as disclosed herein is that they may be transported and stored prior to final formulation, without forming degredation products. The blends of the present invention, e.g. binary blends, therefore provide a commercially viable option for storing the S1P modulator as described herein in stable conditions.

Prior to the surprising findings of the present invention, the instability of the compounds comprising a group Y would not have been able to be safely stored, without the possibility of impurities being formed. With the present invention, the skilled person is now shown which excipients may be used with the S1P modulators for storage and, most importantly, which excipients may be used to reduce the risk of impurities contaminating a final drug product, such impurities being formed by a malliard reaction.

Levels of Impurities Tolerated:

Compositions of the present invention, e.g. binary blends and/or final dosage forms, are preferably free from impurities. It will be understood that the level of impurities tolerated will be judged using pharmaceutically acceptable standards.

However, it is also understood the pharmaceutical standards may only apply to a final dosage form, i.e. the final product. The present invention, in a preferred embodiment provides binary blends containing an S1P receptor modulator as definated herein, i.e. a compound comprising a group of formula Y, which are low, e.g. free, of impurities. Preferably the binary blends of the present invention meet the following criteria for level of impurities:

No more than 4.5 wt % of impurities and/or but no more than 2 wt % for an individual impurity.

Preferably, impurities are at 2 wt % or lower with no individual impurity being more than 0.5 wt %

The "wt %" measurements above are indicators of amount of impurities tolerated. The term "wt %" means the percentage in relation to the amount of the whole formulation, for example 4 wt % means 4 mg in a 100 mg tablet.

Example of Impurity Tolerances, Using the Compound FTY720 as a Reference

There are three qualified degradation products observed in a dosage form: acetyl amide, palmitate amide and stearate amide.

The mechanism for the formation of these degradation products is postulated to be due to a nucleophilic attack of the primary amine of the FTY720 molecule at the carbonyl carbon of the acetic, palmitic or stearic acid.

Based on tox qualification study, the three primary degradation products, acetyl amide, palmitate amide and stearate amide were qualified at levels of 4.6%, 4.5% and 4.8%, respectively.

In order to adequately control the quality and efficacy of the final dosage product each qualified degradation product was assigned a specification of equal to or less than 2.0% of label strength.

The specified degradation products were assigned a specification of equal to or less than 1.0% of label strength.

The unspecified degradation products were assigned a specification of equal to or less than 0.5% of label strength as per the Novartis drug product purity policy.

The sum of all the degradation products above the limit of quantitation (0.1% label strength) was set at equal or less than a total of 4.5%.

FTY720: An Example of a Compound Comprising a Group of Formula Y:

A chemical stability program using binary mixtures of FTY720 and excipients (1% drug substance was stored for 1 month in closed vials at 50° C.) was performed using FTY720 drug substance.

General method to prepare binary mixtures:
1. 10 mg drug substance and 1000 mg excipient were filled into a glass vial (=binary mixture).
2. The closed vials were stored for 1 month at 50° C.

The analytical characterization was performed using gradient HPLC with UV detection. For the analysis, the stored samples were dissolved in 40 ml of 0.0005N hydrochloric acid in isopropanol and stirred with a magnetic stirrer for 30 minutes. This solution was centrifuged and an aliquot of the clear supernatant was used as the test solution.

The limit of quantitation (loq) of the method was 0.1%. The rel. standard deviation $s_{rel}$ of the assay determinations was ≤2%.

| | |
|---|---|
| Apparatus | HPLC system with gradient capability, autosampler and UV detector |
| Column | Waters Xterra ™ MS C$_8$ Length 50 mm, internal diameter 4.6 mm, particle size 2.5 μm, Part number 186000603. |
| Chromatographic conditions | |
| Mobile phase A | 100 mM NaClO$_4$ buffer, pH 2.8:methanol = 93:7 (v/v) |
| Mobile phase B | Acetonitrile |

| Time [min.] | Phase A [%] | Phase B [%] |
|---|---|---|
| 0 | 70 | 30 |
| 1.0 | 70 | 30 |
| 15.0 | 58 | 42 |
| 28.0 | 5 | 95 |
| 30.0 | 5 | 95 |
| 30.1 | 70 | 30 |
| 35.0 | 70 | 30 |

| | |
|---|---|
| Gradient program (linear) | |
| Flow rate | 1.5 ml/min |
| Detection | UV detection at 215 nm |
| Column temperature | 30° C. |
| Auto-sampler Temperature | Ambient |
| Injection volume | 10 μl |
| Run time | 35 min |

The tables below provide a list of potentially feasible excipients including the results of the stability program.

EXAMPLE 1

FTY720 Stability Test with Selected Fillers

| Excipient | Assay in % | Σ impurities in % |
|---|---|---|
| Lactose anhydrous | 101.4 | 0.0 |
| Maize starch | 102.2 | 0.0 |
| Mannitol | 102.3 | 0.0 |
| Mannitol granulated (SD 200) | 99.5 | 0.3 |
| Avicel | 97.9 | 0.2 |
| Citric acid + Mannitol (10 + 90) | 102.4 | 0.0 |
| Sodium hydrogen carbonate + Mannitol (10 + 90) | 102.7 | 0.0 |

EXAMPLE 2

FTY720 Stability Test with Selected Binders

| Excipient | Assay in % | Σ impurities in % |
|---|---|---|
| HPMC 3 cPs | 97.8 | 0.0 |
| HP-Cellulose LH-22 | 99.8 | 0.4 |

EXAMPLE 3

FTY720 Stability Test with Selected Disintegrants

| Excipient | Assay in % | Σ impurities in % |
|---|---|---|
| Maize starch | 102.2 | 0.0 |
| Crosscarmellose sodium | 102.4 | 0.0 |
| Sodium carboxymethylstarch (Primojel) | 103.2 | 0.0 |
| Starch 1500 (Sta RX) | 101.3 | 0.0 |

EXAMPLE 4

FTY720 Stability Test with Selected Lubricants

| Excipient | Assay in % | Σ impurities in % |
|---|---|---|
| Hydrogenated ricinoleic oil (Cutina) | 103.6 | 0.0 |
| Mg stearate + Manitol (1 + 99) | 103.5 | 0.5 |

EXAMPLE 5

FTY720 Stability Test with Selected Flow Regulators

| Excipient | Assay in % | Σ impurities in % |
|---|---|---|
| Aerosil 200 | 101.5 | 0.6 |

EXAMPLE 6

FTY720 Stability Test with Selected Matrix Formers

| Excipient | Assay in % | Σ impurities in % |
|---|---|---|
| Hydroxypropyl methyl cellulose | 97.8 | 0.0 |
| Hydroxypropyl cellulose | 99.8 | 0.4 |
| Methyl cellulose | — | — |
| Ethyl cellulose | — | — |
| Pullulan | — | — |
| Starch, e.g. Pure Cote | 102.2 | 0.0 |
| Povidone | 95.4 | 0.5 |

Polymers having different molecular weights may be used in the same formulation, e.g. having a low and a high molecular weight, i.e. one can use a mixture of e.g. cellulose type polymers having a low and a high MW to provide for different properties.

EXAMPLE 7

FTY720 Stability Test with Selected Plastisizers

| Excipient | Assay in % | Σ impurities in % |
|---|---|---|
| PEG 400 | — | — |
| Dibutyl sebacate | — | — |
| Sorbitol | — | — |

EXAMPLE 8

FTY720 Stability Test with Selected Flavoring Agents

| Excipient | Assay in % | Σ impurities in % |
|---|---|---|
| Menthol | — | — |
| Tutti frutti | | |

EXAMPLE 9

FTY720 Stability Test with Selected Sweeteners

| Excipient | Assay in % | Σ impurities in % |
|---|---|---|
| Sucralose | — | — |
| Sodium saccharine | — | — |

EXAMPLE 10

Non-Feasible Excipients

An example of a non-feasible excipient is shown below. The method to prepare the binary mixtures and the analytical characterization are the same as describe before.

| Excipient | Assay in % | Σ impurities in % |
|---|---|---|
| Glycerylbehenat (Compritol) | 96.2 | >2 |

EXAMPLE 10

S1P Assays

The binding affinity of S1P receptor modulators to individual human S1P receptors may be determined in following assay:

S1P receptor modulator activities of compounds are tested on the human S1P receptors $S1P_1$, $S1P_2$, $S1P_3$, $S1P_4$ and $S1P_5$. Functional receptor activation is assessed by quantifying compound induced GTP [$\gamma$-$^{35}$S] binding to membrane protein prepared from transfected CHO or RH7777 cells stably expressing the appropriate human S1P receptor. The assay technology used is SPA (scintillation proximity based assay). Briefly, DMSO dissolved compounds are serially diluted and added to SPA-bead (Amersham-Pharmacia) immobilised S1P receptor expressing membrane protein (10-20 μg/well) in the presence of 50 mM Hepes, 100 mM NaCl, 10 mM $MgCl_2$, 10 μM GDP, 0.1% fat free BSA and 0.2 nM GTP [$\gamma$-$^{35}$S] (1200 Ci/mmol). After incubation in 96 well microtiterplates at RT for 120 min, unbound GTP [$\gamma$-$^{35}$S] is separated by a centrifugation step. Luminescence of SPA beads triggered by membrane bound GTP [$\gamma$-$^{35}$S] is quantified with a TOPcount plate reader (Packard). $EC_{50}$s are calculated using standard curve fitting software. In this assay, the S1P receptor modulators preferably have a binding affinity to S1P receptor <50 nM.

Preferred S1P receptor modulators are e.g. compounds which in addition to their S1P binding properties also have accelerating lymphocyte homing properties, e.g. compounds which elicit a lymphopenia resulting from a re-distribution, preferably reversible, of lymphocytes from circulation to secondary lymphatic tissue, without evoking a generalized immunosuppression. Naïve cells are sequestered; CD4 and CD8 T-cells and B-cells from the blood are stimulated to migrate into lymph nodes (LN) and Peyer's patches (PP).

The lymphocyte homing property may be measured in following Blood Lymphocyte Depletion assay:

A S1P receptor modulator or the vehicle is administered orally by gavage to rats. Tail blood for hematological monitoring is obtained on day −1 to give the baseline individual values, and at 2, 6, 24, 48 and 72 hours after application. In this assay, the S1P receptor agonist or modulator depletes peripheral blood lymphocytes, e.g. by 50%, when administered at a dose of e.g. <20 mg/kg.

Final Product Manufacture:

The manufacture of final pharmaceutical products may be carried out using conventional techniques. Examples of such techniques are described below, by way of example.

Compressed Tablets

Compressed tablets are exerted to great pressure in order to compact the material. If a sufficiently homogeneous mix of components cannot be obtained with simple mixing, the ingredients must be granulated prior to compression to ensure an even distribution of the active compound in the final tablet. Two basic techniques are used to prepare powders for granulation into a tablet: wet granulation and dry granulation.

Powders that can be mixed well and therefore do not require granulation can be compressed in to a tablet through a technique called Direct Compression.

Lyophilised Tablets

These tablets may be manufactured by way of creating a suspension containing the active ingredient and other excipients, for example Gelatin in an amount, for example, of about 3 wt %, structure forming agents, such as mannitol or sorbitol, for example and in an amount, for example, of about 1.5 wt %, sweeteners and flavouring agents.

An example of a lyophilised tablet formulation is provided below:

The Gelatin/Mannitol solution is cooled to 23° C. and mixed with the active substance. The total solid content is preferably less than 50%. The suspension is then cooled to 15° C. to prevent sedimentation of the suspension before the start of lyophilisation.

Thin Films

The compositions of the present invention may be further mixed with additional excipients to form final products. The final products may be made from the binary compositions using standard techniques, such as the ones below:

Possible manufacturing comprises casting, drawing, extrusion or coating/lamination processes:

Casting is a manufacturing process by which the drug/excipient mixture is introduced into a mold, allowed to solidify within the mold, and then ejected or broken out to make the individual thin film.

Drawing produces a roll by pulling on a molten drug/excipient mixture until it increases in length. This is typically accompanied by a thinning out of the material. The single units are then cut or punched out of these roles and packed, e.g. into pouches.

Extrusion creates rolls by pushing and/or drawing through a die of the desired profile shape. Extrusion may be continuous (producing indefinitely long material) or semi-continuous (producing many short pieces). The single units are then cut or punched out of these roles and packed, e.g. into pouches.

Coating/lamination could be described as manufacturing a laminate first by coating and lamination. The resulting roll is then splitted into smaller rolls. The single units are then cut or punched out of these roles and packed, e.g. into pouches.

According to the invention, the compositions of the present invention, e.g. the final dosage form, are useful for:

a) treatment and prevention of organ or tissue transplant rejection, for example for the treatment of the recipients of heart, lung, combined heart-lung, liver, kidney, pancreatic, skin or corneal transplants, and the prevention of graft-versus-host disease, such as sometimes occurs following bone marrow transplantation; particularly in the treatment of acute or chronic allo- and xenograft rejection or in the transplantation of insulin producing cells, e.g. pancreatic islet cells;

b) treatment and prevention of autoimmune disease or of inflammatory conditions, e.g. multiple sclerosis, arthritis (for example rheumatoid arthritis), inflammatory bowel disease, hepatitis, etc.;

c) treatment and prevention of viral myocarditis and viral diseases caused by viral mycocarditis, including hepatitis and AIDS.

d) treatment and prevention of cancer, e.g. solid tumors, carcinoma, e.g. for preventing metastatic spread of tumours or for preventing or inhibiting growth of micrometastasis By "solid tumors" are meant tumors and/or metastasis (whereever located) other than lymphatic cancer, e.g. brain and other central nervous system tumors (eg. tumors of the meninges, brain, spinal cord, cranial nerves and other parts of central nervous system, e.g. glioblastomas or medulla blastomas); head and/or neck cancer; breast tumors; circulatory system tumors (e.g. heart, mediastinum and pleura, and other intrathoracic organs, vascular tumors and tumor-associated vascular tissue); excretory system tumors (e.g. kidney, renal pelvis, ureter, bladder, other and unspecified urinary organs); gastrointestinal tract tumors (e.g. oesophagus, stomach, small intestine, colon, colorectal, rectosigmoid junction, rectum, anus and anal canal), tumors involving the liver and intrahepatic bile ducts, gall bladder, other and unspecified parts of biliary tract, pancreas, other and digestive organs); oral cavity (lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx); reproductive system tumors (e.g. vulva, vagina, Cervix uteri, Corpus uteri, uterus, ovary, and other sites associated with female genital organs, placenta, penis, prostate, testis, and other sites associated with male genital organs); respiratory tract tumors (e.g. nasal cavity and middle ear, accessory sinuses, larynx, trachea, bronchus and lung, e.g. small cell lung cancer or non-small cell lung cancer); skeletal system tumors (e.g. bone and articular cartilage of limbs, bone articular cartilage and other sites); skin tumors (e.g. malignant melanoma of the skin, non-melanoma skin cancer, basal cell carcinoma of skin, squamous cell carcinoma of skin, mesothelioma, Kaposi's sarcoma); and tumors involving other tissues inicluing peripheral nerves and autonomic nervous system, connective and soft tissue, retroperitoneum and peritoneum, eye and adnexa, thyroid, adrenal gland and other endocrine glands and related structures, secondary and unspecified malignant neoplasm of lymph nodes, secondary malignant neoplasm of respiratory and digestive systems and secondary malignant neoplasm of other sites.

Where hereinbefore and subsequently a tumor, a tumor disease, a carcinoma or a cancer is mentioned, also metastasis in the original organ or tissue and/or in any other location are implied alternatively or in addition, whatever the location of the tumor and/or metastasis is.

Accordingly, in further aspects the present invention provides:

1. A composition as defined above, for use in treating or preventing a disease or condition as defined above.
2. A method of treating a subject in need of immunomodulation, comprising administering to the subject an effective amount of a composition as defined above.
3. A method of treating or preventing a disease or condition as defined above, comprising administering to the subject a composition as defined above.
4. Use of a pharmaceutical composition as defined above for the preparation of a medicament for the prevention or treatment of a disease or condition as defined above.

The invention claimed is:

1. A stable pharmaceutical composition for oral administration comprising:
   (i) a compound selected from 2-amino-2-[2-(4-octylphenyl)ethyl]propane-1,3-diol in free form, a pharmaceutically acceptable salt thereof, 2-amino-2-[2-(4-octylphenyl)ethyl]propane-1,3-diol-phosphate, 1-{4-[1-(4-cyclohexyl-3-trifluoromethyl-benzyloxyimino)-ethyl]-2-ethyl-benzyl}-azetidine-3-carboxylic acid, and
   (ii) one or more of the following excipients:
   (a) one or more Fillers selected from the group consisting of Lactose monohydrate, Lactose anhydrous, Maize starch, sucrose, and Microcrystalline cellulose, citric acid and sodium hydrogen carbonate;
   (b) one or more Binders selected from the group consisting of HPMC, and HPC;
   (c) one or more Disintegrants selected from the group consisting of Maize starch, Croscarmellose sodium, Sodium carboxymethylstarch, and pregelatinized;
   (d) one or more Lubricants selected from the group consisting of Hydrogenated castor oil and magnesium stearate;
   (e) a Flow regulator that is Colloidal silicone dioxide;
   (f) one or more Matrix formers selected from the group consisting of Hydroxypropyl methyl cellulose, Hydroxypropyl cellulose, Starch and Povidone.

2. A composition according to claim 1, wherein the excipients are selected from the group consisting of Lactose, microcrystalline cellulose, HPMC, HPC, Crospovidone, croscarmellose sodium, starch, colloidal silicone dioxide, and magnesium stearate.

3. The composition of claim 1, wherein the composition comprises a binary blend consisting of a compound selected from 2-amino-2-[2-(4-octylphenyl) ethyl]propane-1,3-diol in free form, a pharmaceutically acceptable salt thereof, 2-amino-2-[2-(4-octylphenyl)ethyl]propane-1,3-diol-phosphate, 1-{4-[1-(4-cyclohexyl-3-trifluoromethyl-benzyloxyimino)-ethyl]-2-ethyl-benzyl}-azetidine-3-carboxylic acid, and one excipient.

4. The composition of, claim 1 wherein said is selected from the group consisting of 2-amino-2-[2-(4-octylphenyl)ethyl]propane-1,3-diol (FTY720) in free form, a pharmaceutically acceptable salt thereof, a prodrug thereof, and FTY720.

5. The composition of claim 3, wherein the level of impurities is not more than 4.5 wt % and/or no individual impurity has a percentage greater than 2 wt %.

6. A composition according to claim 1, in the form of a tablet or capsule.

7. The composition of claim 4 wherein the compound containing a group of formula Y is FTY 720 in free form or a pharmaceutically acceptable salt thereof.

8. A composition according to claim 3, wherein the excipient is Lactose anhydrous.

9. A composition according to claim 3, wherein the excipient is selected from starch, croscarmellose sodium, and sodium carboxymethylstarch.

10. A composition according to claim 3, wherein the excipient is selected from Microcrystalline cellulose, HPMC and HP-Cellulose.

11. A composition according to claim 3, wherein the excipient is selected from colloidal silicone dioxide, methyl cellulose, ethyl cellulose and povidone.

12. A composition according to claim 3, wherein the excipient is hydrogenated castor oil.

13. A composition according to claim 3, wherein the level of any individual impurity measured by HPLC with UV detection is not more than 0.5 wt %.

* * * * *